United States Patent [19]

Aichinger et al.

[11] Patent Number: 5,446,780
[45] Date of Patent: Aug. 29, 1995

[54] X-RAY APPARATUS WITH MECHANICAL DISTANCE-MEASURING DEVICE

[75] Inventors: Horst Aichinger, Fuerth; Thomas Schmitt, Forchheim, both of Germany

[73] Assignee: Siemens Aktiengesellschaft, Munich, Germany

[21] Appl. No.: 202,018

[22] Filed: Mar. 25, 1994

[30] Foreign Application Priority Data

May 5, 1993 [DE] Germany .................. 43 14 897.2

[51] Int. Cl.6 .............................................. A61B 10/00
[52] U.S. Cl. ...................................... 378/204; 378/97; 378/108
[58] Field of Search .............. 378/204, 205, 210, 145, 378/151, 150, 96, 97, 108, 110, 109, 111, 112, 117, 118

[56] References Cited

U.S. PATENT DOCUMENTS

| | | | |
|---|---|---|---|
| 3,502,878 | 3/1970 | Stewart | 250/105 |
| 4,027,166 | 5/1977 | Aichinger et al. | 250/416 |
| 4,060,733 | 11/1977 | Franke et al. | 378/206 |
| 4,896,343 | 1/1990 | Saunders | 378/206 |

FOREIGN PATENT DOCUMENTS

GM1677067 2/1954 Germany .
OS2421243 7/1980 Germany .

Primary Examiner—David P. Porta
Assistant Examiner—Don Wong
Attorney, Agent, or Firm—Hill, Steadman & Simpson

[57] ABSTRACT

An x-ray apparatus includes an x-ray tube having a focus, the x-ray tube being contained in a housing and the housing having a mechanical distance-measuring device attache thereto. The mechanical distance-measuring device is suitable for obtaining a measured value which exactly corresponds to the focus-to-skin distance for all types of examinations. The mechanical distance-measuring device, which may be a tape measure, is connected to an electrical signal generator which converts the mechanically measured value into a corresponding electrical signal.

5 Claims, 1 Drawing Sheet

X-RAY APPARATUS WITH MECHANICAL DISTANCE-MEASURING DEVICE

BACKGROUND OF THE INVENTION

1. Field of the Invention

The present invention is directed to an x-ray apparatus of the type having means for measuring the focus-to-skin distance.

2. Description of the Prior Art

Many radiation protection regulations, which regulate the operation of radiographic and fluoroscopic installations, require an identification of the incident radiation dosage to which a patient is exposed, in order to evaluate the radiation risk to the patient. The incident radiation dosage is the radiation dose present at the surface (i.e., the skin, of the patient). The incident dosage can be calculated in theory using a measuring arrangement including a radiation detector (actinometer) with two measurement fields (areas) arranged concentrically relative to each other, when the focus-to-skin distance is known. The radiation detector is attached to the diaphragm housing of the primary radiation diaphragm of the x-ray apparatus, as disclosed in German OS 24 21 243, so that the relative location of the measurement fields with respect to the focus is known. The incident dosage is obtained by processing the output signals of the two measurement fields in combination an electrical signal corresponding to the focus-to-skin distance. This electrical signal is conventionally obtained using infrared or ultrasound measuring instruments. These types of measuring instruments, however, cannot be used, for example, when the patient is covered with sheets.

SUMMARY OF THE INVENTION

It is an object of the present invention to provide an x-ray apparatus having means for obtaining the focus-to-skin distance with a high precision, during all types of examination conditions, and for obtaining an electrical signal corresponding to the focus-to-skin distance.

The above object is achieved in accordance with the principles of the present invention wherein a mechanical distance-measuring device is disposed at a known location relative to the focus of the x-ray tube, so that a focus-to-skin distance can be obtained based on a mechanical measurement of the distance from the measuring device to the skin of the patient. Means are also provided for converting the mechanically measured distance into a corresponding electrical signal.

In a preferred embodiment of the invention, the mechanical distance-measuring device is a tape measure, and the tape measure is disposed in the housing for the primary radiation diaphragm. The tape measure is coupled to a measured value pick-up means, such a potentiometer, which converts the mechanically measured value into an electrical signal. The pick-up means can be supplied, for example, with an offset voltage, which is always superimposed on its output, so as to take into account the fact that the locations of the tape measure and the focus do not exactly coincide; the offset voltage corresponding to the fixed distance between the focus and the tape measure.

The output signal from the pick-up means is then processed on combination with values obtained from two concentric measuring fields of a radiation detector, in order to form an electrical signal corresponding to the incident dosage.

DESCRIPTION OF THE PREFERRED EMBODIMENTS

Figure 1:
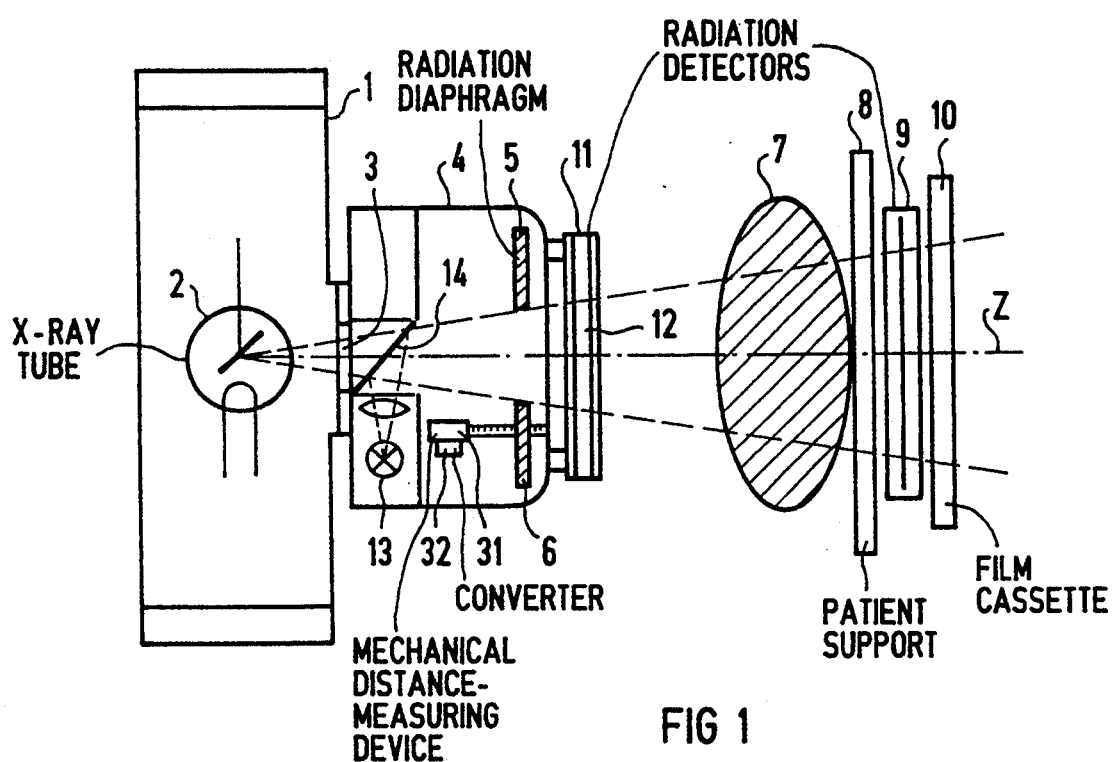
FIG. 1 is a side schematic view, partly in section, of an x-ray apparatus with a mechanical distance-measuring device constructed in accordance with the principles of the present invention.

In the embodiment of the apparatus shown in FIG. 1, an x-ray tube 2 is contained in a housing 1, the x-ray tube 2 being supplied with high-voltage and a filament current by a supply (not shown) in a known manner. X-rays emerge from the housing 1 through a radiation exit window 3, and penetrate a diaphragm housing 4, in which diaphragm plates 5 and 6 are arranged for gating the radiation field. The gated field is incident on a patient 7 lying on a support 8, for obtaining an exposure of a selected region of the patient 7. After penetrating the patient 7, the x-rays are incident on a measurement chamber 9 of an automatic exposure unit, and also are incident on a cassette 10 containing x-ray film.

Only the two diaphragm plates 5 and 6 which limit the x-ray beam in one direction are visible in FIG. 1. It will be understood that the x-ray beam is limited in a direction perpendicular thereto (i.e., perpendicular to the plane of the drawing) with two further diaphragm plates.

A further housing 11 is attached to the diaphragm housing 4, which contains a radiation detector 12, described in more detail below.

The apparatus shown in FIG. 1 is also provided with a light-beam localizer, which illuminates the gated radiation field in a known manner so as to permit the boundary of the field to be visually recognized. This light-beam localizer includes a light source 13 disposed in the diaphragm housing 4, which generates a light beam through a lens, which is directed by a mirror 14 through the exit opening of the diaphragm housing 4. The mirror 14 is transmissive to x-rays.

The apparatus also includes a mechanical distance-measuring device 31, which in the embodiment of FIG. 1 is a tape measure, arranged in or on the diaphragm housing 4. The tape of the mechanical distance-measuring device 31 can be withdrawn from the diaphragm housing 4 in the direction of a central ray Z of the x-ray beam generated by the x-ray tube 2, until the end of the tape touches the patient 7. A converter 32 is coupled to the mechanical distance-measuring device 31 and converts the mechanically measured value into a corresponding electrical signal. Since the mechanical distance-measuring device 31 is to be used for the purpose of measuring the focus-to-skin distance, and since the device 31 is not coincident with the position of the focus of the x-ray tube 2, the converter 32 can be provided with an offset signal, such an offset voltage, corresponding to the fixed distance between the device 31 and the focus of the x-ray tube 2. When the device 31 measures a distance of zero (i.e., when the tape thereof has not been withdrawn at all), the converter 32 will still generate an output signal corresponding to the aforementioned fixed distance.

Figure 2:
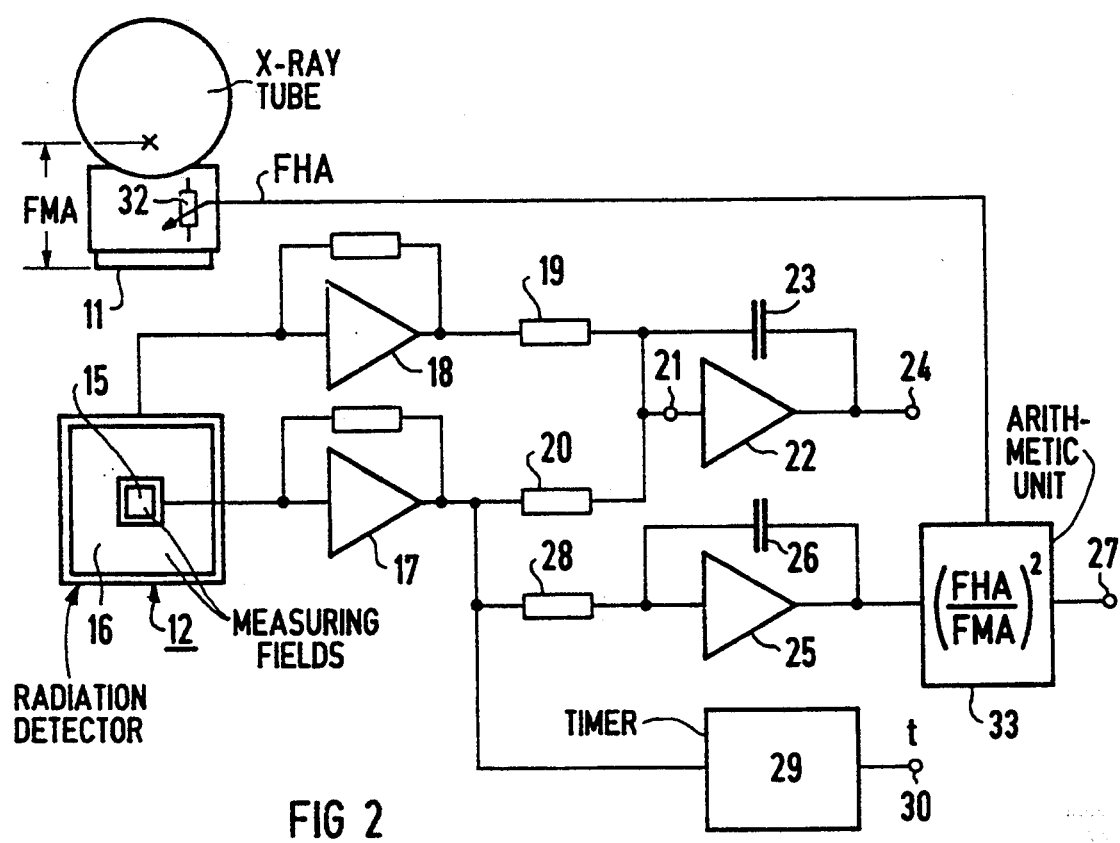
FIG. 2 is a simplified circuit schematic diagram for the x-ray apparatus of FIG. 1.

As shown in FIG. 2, the radiation detector 12 has two measurement fields (areas) 15 and 16, disposed concentrically relative to each other. The field 15 is dimensioned so that it lies completely within the x-ray beam generated by the x-ray tube 2, given the narrowest gating of the diaphragm. The field 16, by contrast, is dimensioned so that it will acquire all of the x-rays emerging from the primary radiation diaphragm given the largest gating, and such that the portion of the field 16 penetrated by the x-rays corresponds to the size of the radiation field due to the selected gating.

The output signal of the field 15 is amplified in an amplifier 17, and the output signal of the field 16 is amplified in an amplifier 18. The respective amplified output signals are supplied via two coupling resistors to the input 21 of a further amplifier 22, which functions as an integrator in combination with a capacitor 23. The respective outputs of the amplifiers 17 and 18 are added at the input 21. A signal which is dependent on the dose rate, and on the size of the gated field, is thus present at the input 21. After integration of this signal in the integrator formed by the amplifier 22 and the capacitor 23, a signal representative of the area/dose product is present at the output 24.

The output signal of the amplifier 17 is dependent on the existing dose rate, but not on the size of the field which has been gated. After amplification in another amplifier 25, having an integration capacitor 26, a signal is obtained which is supplied to an arithmetic unit 33, which generates an output signal corresponding to the incident dosage, in the manner described below. The output of the amplifier 17 is coupled to the integrator formed by the amplifier 25 and the capacitor 26 by means of a coupling resistor 28.

The reason why the output signal of the amplifier 17 is dependent only on the dose rate, and is not dependent on the field size, is because the measurement field 15 is fully penetrated by the x-ray beam, even given the smallest gating setting. The output signal of the amplifier 17 can therefore also be used to control a timer 29, which is started upon the appearance of x-rays, and supplies a signal at its output 30 which represents the time during which the x-ray beam is present, i.e., the irradiation time.

The respective signals at the outputs 24, 27 and 30 can be used to control display instruments for displaying the quantities of area/dose product, incident dose and irradiation time.

The measurement fields 15 and 16 are disposed concentrically in a common plane, and thus can be accommodated in a single housing, such as the housing 11 shown in FIG. 1.

The output signal of the amplifier 25, in exact terms, represents the diaphragm output dose. The incident dosage can be calculated therefrom, however, in the arithmetic unit 33 multiplying the output signal of the amplifier 25 (i.e., the output signal of the integrator formed by the amplifier 25 and the capacitor 26) by the square of the quotient of the focus-to-subject distance (measured value FHA) and the focus-to-measuring field distance (constant FMA). The signal corresponding to the incident dosage is thus formed at the output 27 of the arithmetic unit 33.

The amplifiers 17 and 18 function as current-to-voltage converters in the exemplary embodiment of FIG. 2. There, output voltage are proportional to the ionization currents which are present in the measurement fields 15 and 16.

The timer 29 must be returned to its zero position at the end of an irradiation exposure. Moreover, the integrators formed by the amplifier 22 and the capacitor 23, and by the amplifier 25 and the capacitor 26, must be reset. Such zeroing and resetting can either ensue manually or automatically after the output signals of the measuring apparatus have been obtained if the capacitors 23 and 26 are respectively replaced by resistors, the quantities of dose/area product rate or incident dosage rate can alternatively be measured at the respective outputs 24 and 27.

Other mechanical distance-measuring devices 31 may be employed, for example, an extensible telescoping rod, instead of the aforementioned tape measure.

A push button can be provided at the diaphragm housing 4 to inform the attendant making the mechanical measurement that the electronic signal corresponding thereto has been obtained and the necessary processing has been completed, thereby informing the attendant that the tape of the tape measure can be retracted so that the remainder of the examination will not impeded.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray apparatus for examining a patient comprising:

x-ray means for irradiating said patient with an x-ray beam emanating from said focus and having a central ray, said x-ray means having an x-ray means housing;

mechanical distance-measuring means extensible along said central ray for mechanically measuring a distance from said x-ray means housing; and converter means for converting the distance mechanically measured by said mechanical distance-measuring means into an electrical signal.

2. An x-ray apparatus as claimed in claim 1 wherein said mechanical distance-measuring means is a tape measure.

3. An x-ray apparatus as claimed in claim 1 wherein said x-ray means includes a primary radiation diaphragm for gating said x-ray beam and a primary radiation diaphragm housing which is a part of said x-ray means housing, and wherein said mechanical distance-measuring means is disposed in said primary radiation diaphragm housing.

4. An x-ray apparatus as claimed in claim 1 wherein said converter means comprises means for converting the mechanical distance measured by said mechanical distance-measuring means into an electrical signal corresponding to a focus-to-skin distance between said focus and said subject.

5. An x-ray apparatus as claimed in claim 1 wherein said x-ray means includes a primary radiation diaphragm for gating said x-ray beam to selectably set an x-ray beam size between a minimum x-ray beam size and a maximum x-ray beam size, and a primary radiation diaphragm housing which is a part of said x-ray means housing, and wherein said converter means comprises means for converting the mechanical distance measured by said mechanical distance-measuring means into an electrical signal corresponding to a focus-to-skin distance between said focus and said subject, and said x-ray apparatus further comprising:

a radiation detector disposed at said primary radiation diaphragm housing, said radiation detector having first measuring field means of a size for acquiring radiation from all of said x-ray beam emerging from said primary radiation diaphragm even given said maximum x-ray beam size and for generating a first electrical signal corresponding to the radiation incident on said first measuring field means, and second measuring field means of a size always fully penetrated by radiation from said x-ray beam even given said minimum x-ray beam size for generating a second signal corresponding to the radiation incident on said second measuring field means, said first and second measuring field means being disposed concentrically relative to each other in a common plane;

means for adding said first and second signals for forming a signal corresponding to the area/dose product;

means for integrating said second signal to form an integrated signal; and arithmetic means, supplied with said integrated signal and with said signal corresponding to the focus-to-skin distance, for forming an output signal corresponding to the incident radiation dosage on said subject by multiplying said integrated signal by the square of the quotient of said focus-to-skin distance and a constant distance between said focus and said common plane.

* * * * *